United States Patent [19]
Everett et al.

[11] Patent Number: 6,164,280
[45] Date of Patent: *Dec. 26, 2000

[54] APPLYING HIGH ENERGY LIGHT AND HEAT FOR GYNECOLOGICAL STERILIZATION PROCEDURES

[75] Inventors: Royice B. Everett, Edmond, Okla.; Johnny M. Bruce, Magnolia, Tex.

[73] Assignee: MyriadLase, Inc., Mansfield, Tex.

[ * ] Notice: This patent is subject to a terminal disclaimer.

[21] Appl. No.: 08/882,562

[22] Filed: Jul. 3, 1997

Related U.S. Application Data

[60] Division of application No. 08/343,093, Nov. 21, 1994, Pat. No. 5,897,551, which is a continuation-in-part of application No. 08/155,091, Nov. 19, 1993, abandoned, which is a continuation of application No. 07/895,940, Jun. 9, 1992, abandoned, which is a continuation of application No. 07/498,349, Mar. 23, 1990, Pat. No. 5,147,353.

[51] Int. Cl.⁷ ................................................. A61B 19/00
[52] U.S. Cl. ............................... 128/898; 606/15; 607/89; 600/33
[58] Field of Search ............................. 128/898; 600/33; 606/2, 14, 15, 28, 27, 11, 12, 135, 193, 29; 607/89

[56] References Cited

U.S. PATENT DOCUMENTS

| | | | |
|---|---|---|---|
| 5,140,984 | 8/1992 | Dew et al. | 607/89 |
| 5,147,353 | 9/1992 | Everett | 606/15 |

*Primary Examiner*—V. Millin
*Assistant Examiner*—Kelly O'Hara
*Attorney, Agent, or Firm*—McAfee & Taft

[57] ABSTRACT

A localized heat applying medical device is provided for applying heat to tissue adjacent a patient's tubal ostia in order to close the patient's fallopian tubes and sterilize the patient. Procedures of performing sterilizations are also disclosed.

17 Claims, 6 Drawing Sheets

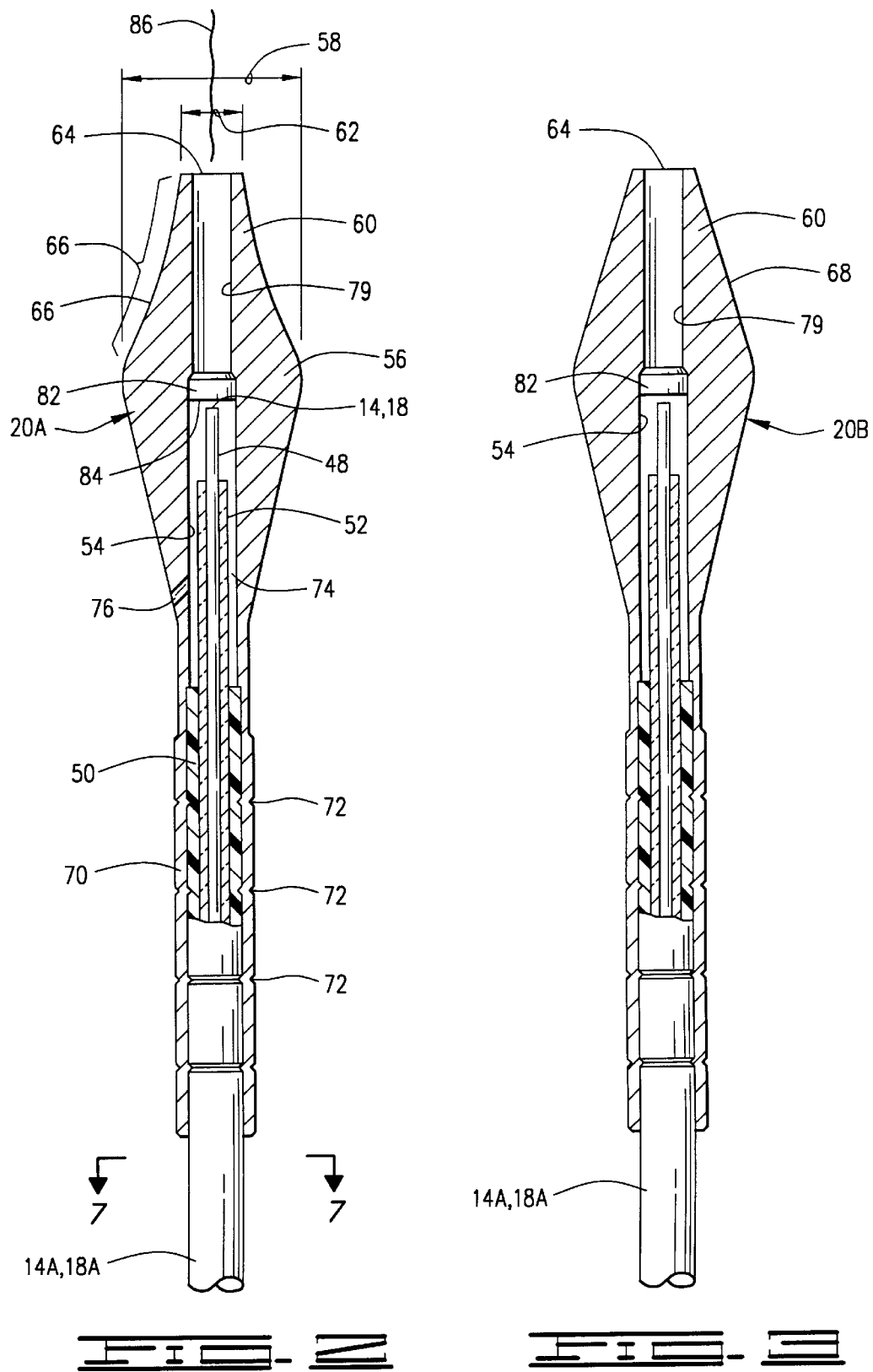

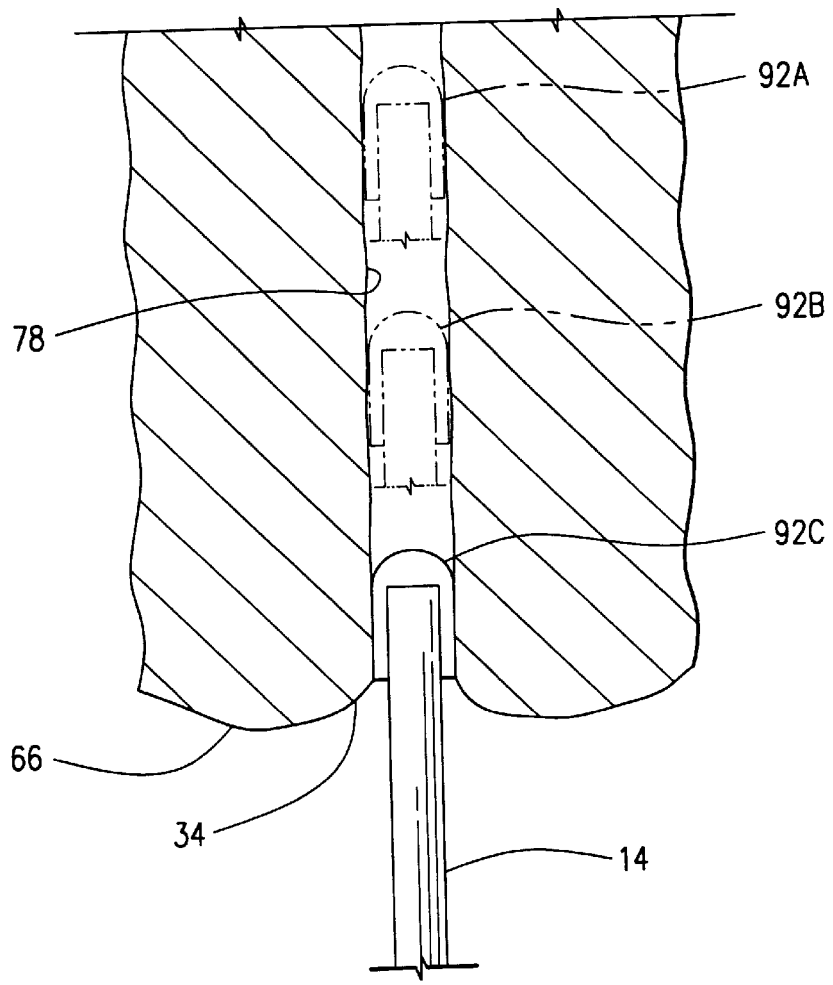
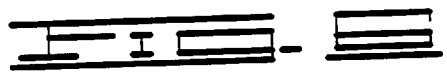
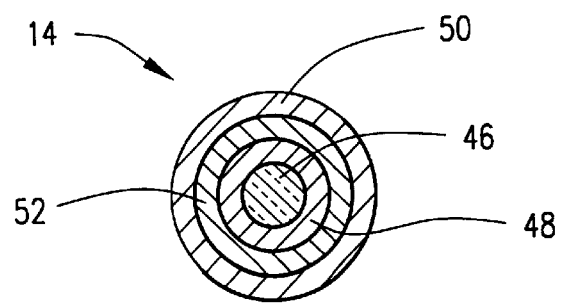
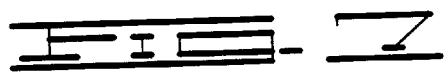

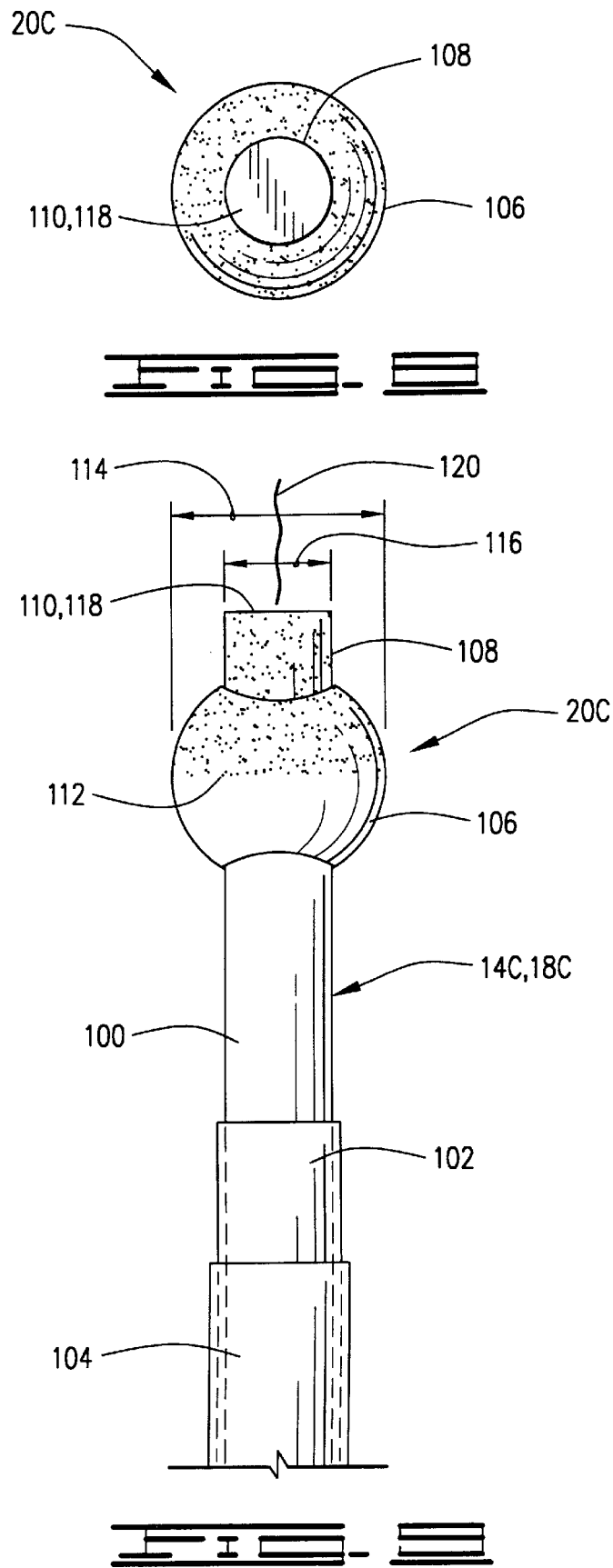

APPLYING HIGH ENERGY LIGHT AND HEAT FOR GYNECOLOGICAL STERILIZATION PROCEDURES

This is a divisional of application Ser. No. 08/343,093, filed Nov. 21, 1994, now U.S. Pat. No. 5,897,551, which is a continuation in part of application Ser. No. 08/155,091, filed Nov. 19, 1993, abandoned, which is a continuation of application Ser. No. 07/895,940, filed Jun. 9, 1992, abandoned, which is a continuation of application Ser. No. 07/498,349, filed Mar. 23, 1990, now U.S. Pat. No. 5,147,353.

This is a continuation-in-part of co-pending application Ser. No. 08/155,091 filed on Nov. 19, 1993, which is a continuation of Ser. No. 07/895,940 filed on Jun. 9, 1992, now abandoned, which is a continuation of Ser. No. 07/498,349 filed on Mar. 23, 1990, now U.S. Pat. No. 5,147,353.

BACKGROUND OF THE INVENTION

1. Field of the Invention

The present invention relates to medical devices and procedures for applying localized heat to a site in the patient's body, particularly for purposes such as sterilization of a female patient by closing of the fallopian tubes.

2. Description of the Prior Art

The prior art includes devices and procedures for applying localized heat to a site in a patient's body for a number of purposes, generally including altering, removing or destroying tissue in the patient's body.

U.S. Pat. Nos. 4,773,413 and 4,662,368 both to Hussein et al. disclose a localized heat applying medical device powered by laser energy transmitted through an elongated conduit. The heat applying device includes a bulbous heat generating element, having an aperture in the forward end of the device permitting a portion of the laser energy to be transmitted out the aperture and directly applied to the patient's body tissue. The devices disclosed in Hussein et al. are particularly designed for use in treating cardiovascular disease by removing arteriosclerotic deposits from blood vessels. Commercial embodiments of the Hussein et al. device are marketed by LaserControl Medical Systems Division of Trimedyne, Inc., of Santa Ana, Calif. One such commercially available device is marketed as the SpectraProbe™-80, which is designed such that approximately eighty percent of the laser energy transmitted thereto is emitted through the optical aperture of the end of the device. The SpectraProbe™-80 has a tip diameter of about 2.5 millimeters.

German Patent No. 2,826,383, published Dec. 20, 1979, of Eichler, et al., discloses a laser probe placed directly against or inserted into the patient's tissue for treating the same.

It is also known to use laser powered devices in hysteroscopic procedures. For example, a surgical procedure referred to as an "endometrial ablation" has been recently developed as an alternative to hysterectomy for treatment of excessive uterine bleeding. In this procedure, an Nd:YAG laser is used to destroy the entire endometrium lining the uterus. An optical fiber is inserted in the uterus by means of a hysteroscope to conduct the laser energy to the endometrium. With the aid of a parallel optical viewing fiber of the hysteroscope, the end of the laser transmitting fiber is slowly moved across the surface of the endometrium so that the laser energy penetrates and destroys the endometrium so that the laser energy penetrates and destroys the endometrium which is on the order of three millimeters thick. Typical prior art procedures have utilized a bare optical fiber for transmitting the laser energy. Two techniques have been developed. By one technique, the end of the bare optic fiber is actually touched to the endometrium in a "dragging" procedure. By a second technique, generally referred to as "blanching", the bare tip of the optic fiber is held several millimeters away from the endometrium. These techniques are generally described in Daniell et al., "Photodynamic Ablation of the Endometrium with the ND:YAG Laser Hysteroscopically as a Treatment of Menorrhagia", *Colposcopy and Gynecologic Laser Surgery*, Volume 2, No. 1, 1986; Mackety, "Alternative to Hysterectomy: Endometrial Ablation by Laser Photovaporization", *Today's OR Nurse*, Volume 8, No. 4; and Goldrath et al., "Laser Photovaporization of Endometrium for the Treatment of Menorrhagia", *Am. J. Obstet. Gynecol.*, Volume 140, No. 1, page 14, May 1, 1981.

The Goldrath et al. and Daniell et al. articles cited above, both suggest that patients undergoing an endometrial ablation procedure will probably be sterile following the procedure. The work of Goldrath et al. and Daniell et al. was not directed to the end purpose of sterilization, but it was observed as a side effect of the treatment. For reasons further described herein, it is believed that the cause of the sterility observed by Goldrath et al. and Daniell et al. was the destruction of the patient's endometrium.

A recent improvement upon the endometrial ablation procedure, wherein a heat generating tip is attached to the end of the laser transmitting conduit, with the tip being designed to laterally emit a portion of the laser energy is disclosed in Everett et al. pending Application No. PCT/US89/02492 filed Jun. 7, 1989, which has been published in INTERNATIONAL PUBLICATION NO. WO 89/11834 on Dec. 14, 1989. That application is a continuation-in-part of U.S. patent application Ser. No. 07/205,218 filed Jun. 10, 1988.

In all of the endometrial ablation procedures set forth in the references discussed above, the treatment is directed to the endometrium, that is the lining of the uterine cavity, for the purpose of destroying that lining to prevent excessive bleeding. The procedures are not directed to the purpose of closing the fallopian tubes to induce sterilization. Furthermore, the endometrial ablation procedures do not involve any substantial fixed contact of the tip of the laser fiber, or of a heating device on the end of the laser fiber, with the tissue, but rather involve a continuous movement of the tip while dragging it across, or moving it while held a slight distance away from, the tissue.

SUMMARY OF THE INVENTION

The present invention provides procedures for sterilizing patients by the use of heat and laser light energy by holding a heating device in fixed contact with tissue adjacent the tubal ostia in order to coagulate the interstitial portion of the fallopian tubes, thereby closing the fallopian tubes. Localized heat applying devices are provided which are particularly adapted for use in such procedures.

A localized heat applying medical device of the invention for applying heat to the tissue adjacent a patient's tubal ostia in order the close the patient's fallopian tubes and sterilize the patient includes an elongated light transmitting conduit having a proximal end and a distal end. On the distal end of the light transmitting conduit is a heat application means for applying the heat to the tissue. In some embodiments, the heat application means comprises a bulbous heat generating means which is mounted on the distal end of the conduit and adapted for converting light energy transmitted by the conduit in part to heat, thereby raising the temperature thereof. In another embodiment, the heat application means comprises a modified tip on the light transmitting conduit which itself is not heated but which is used to apply only radiant energy transmitting by the conduit to heat the tissue.

In first and second embodiments, the heat application means includes the bulbous heat generating means which has a larger portion with an outside diameter of at least about two millimeters, and has a tapered forward portion with a forwardmost tip having an outside diameter no greater than about one millimeter, so that the tip can be received through one of the tubal ostia with the larger portion of the bulbous heat generating means engaging an inner wall of the patient's uterus adjacent said one of the tubal ostia. This embodiment of the bulbous heat generating means includes a light transmitting aperture means. extending through the tapered forward portion of the tip for enabling light energy transmitted by the conduit in part to pass through the aperture means into the fallopian tube associated with said one of the tubal ostia.

In a third embodiment, the heat application means is integral with the distal end of the light transmitting conduit and comprises an enlarged orb portion formed thereon with an outside diameter of at least about two millimeters. Preferably, but not by way of limitation, the third embodiment also comprises an elongated portion extending therefrom with a forwardmost tip having an outside diameter no greater than about one millimeter, so that the tip can be received through said one of the tubal ostia with the orb portion engaging an inner wall of the patient's uterus adjacent said one of the tubal ostia. A forwardly facing portion of the orb and the outer cylindrical surface of the tip are preferably frosted while the forwardmost end of the tip defines a clear or polished light transmitting aperture means for enabling light energy transmitted by the conduit in part to pass through the aperture means into the fallopian tube associated with said one of the tubal ostia. The frosted portion transfers some light energy therethrough to heat the adjacent portion of said one of the tubal ostia in contact therewith, but does not itself significantly heat up.

Alternatively, the third embodiment may comprise only the enlarged orb portion with a clear or polished light aperture means thereon without an elongated portion. In such a configuration, the forwardly facing portion of the orb, except for the aperture means, is preferably frosted.

Procedures utilizing such devices include steps of inserting into the patient's uterus the elongated laser light energy transmitting conduit having the heat generating device on the distal end thereof. Then the heat generating device is maintained in fixed contact with the inner wall of the patient's uterus adjacent the tubal ostia for a sufficient time and while transmitting sufficient energy to the light generating device to coagulate a substantial part of the interstitial portion of the patient's fallopian tubes to close the same.

Numerous objects, features and advantages of the present invention will be readily apparent to those skilled in the art upon a reading of the following disclosure when taken in conjunction with the accompanying drawings.

BRIEF DESCRIPTION OF THE DRAWINGS

FIG. 2 is a cross-sectional illustration of a first preferred embodiment of the heat applying device connected to the distal end of the laser transmitting conduit and having a tapered forward end with a concave profile.

FIG. 3 is a view similar to FIG. 2 of a second preferred embodiment of the heat applying device, having a frusto-conical tapered forward end.

FIG. 6 is a schematic illustration of a procedure utilizing a cylindrical heat generating means like that of FIG. 5 in a procedure wherein it is completely inserted into the interstitial portion of the fallopian tube and then sequentially heated at different locations.

FIG. 7 is a cross-sectional view taken along lines 7—7 of FIG. 2.

FIG. 8 is a distal end elevational view of a third preferred embodiment of the heat applying device.

FIG. 9 is a side elevational illustration of the third preferred embodiment of the heat applying device and showing a generally cylindrical light transmitting conduit with an integrally formed orb portion.

DETAILED DESCRIPTION OF THE PREFERRED EMBODIMENTS

The present invention is a medical device for applying localized heat to tissue adjacent a patient's tubal ostia in order to close the patient's fallopian tubes in the area of the interstitial portion of the fallopian tubes and to thereby sterilize the patient.

Figure 1:
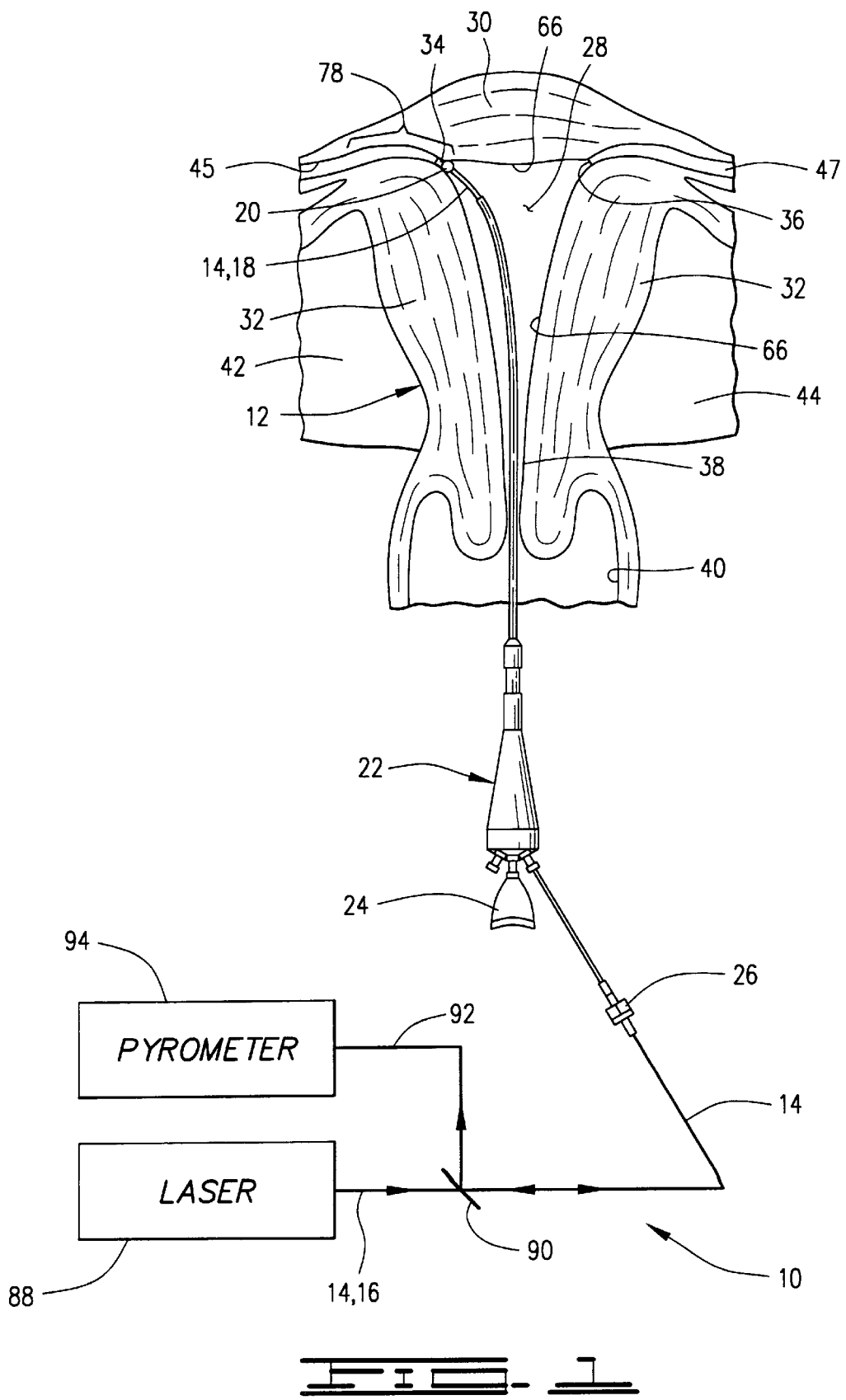
FIG. 1 is a schematic illustration including a cross-sectional view of the anatomy of the patient's uterus, with a localized heat applying device held in place therein by means of a hysteroscope with which is associated a laser energy source.

Referring to FIG. 1, a medical device 10 embodying the present invention is shown positioned within uterus 12 of a human female patient. Device 10 includes an elongated light transmitting conduit 14 having a proximal end 16 and a distal end 18. In the particular preferred embodiment disclosed, conduit 14 is an optical fiber for transmitting laser light energy.

The device 10 further includes a heat application means, generally designated by the numeral 20, on the distal end 18 of conduit 14 for converting light energy transmittal by the conduit 14 whereby localized heat may be applied to a desired portion of the patient's tissue.

The device 10 includes a conventional hysteroscope 22 which carries the light transmitting conduit 14, a parallel optical viewing fiber (not shown), and parallel fluid flow conduits (not shown). The hysteroscope 22 permits a position to view the placement of the heat application means 20 through the parallel optical viewing fiber. This can be observed through the eyepiece of the hysteroscope 22. The hysteroscope 22 includes a connector 26 for linking with the light transmitting conduit 14. The hysteroscope 22 is inserted in a fluid medium such as saline solution which has been placed within the uterine cavity 28.

In FIG. 1, the device 10 is shown positioned within the patient's uterine cavity 28 which is defined by an upper fundus 30 and a somewhat cylindrical side wall 32. The side wall 32 can generally be defined as extending downwardly from the tubal ostia 34 and 36 to the internal cervical os 38. Tubal ostia 34 and 36 communicate the uterine cavity 28 with the patient's fallopian tubes 45 and 47. The device 10 is inserted as part of the hysteroscope 22 into the uterus 12 via vaginal canal 40 and through the internal cervical os 38 using appropriate dilation procedures. The body or side wall 32 of the uterus 12 is supported by broad ligaments 42 and 44.

A first preferred embodiment of the heat application means 20 is shown in FIG. 2 and characterized by a bulbous heat generating means 20A connected to the distal end 18 of light transmitting conduit 14. A second preferred embodiment of the heat application means 20 is shown in FIG. 3. The second embodiment of the heat application means 20 is similar to the first and is characterized by a bulbous heat generating means designated by the numeral 20B.

The heat generating means 20A and 20B are modified forms of the heat generating means shown and described in U.S. Pat. No. 4,773,413 of Hussein et al., and particularly, the heat generating means 20A and 20B are modified forms of the device shown in FIG. 10 of U.S. Pat. No. 4,773,413. The details of construction of such heat generating means as generally described in U.S. Pat. No. 4,773,413 are incorporated herein by reference. The heat generating means 20A and 20B have been modified as compared to those of the prior art by changing their external geometry to make them more appropriate for use in the procedures disclosed herein.

A third preferred embodiment of the heat application means 20 is shown in FIGS. 8 and 9 and designated by numeral 20C. The heat application means 20C is integrally formed with the distal end 18 of the light transmitting conduit 14. This third embodiment heat application means 20C has a unique construction which is specifically designed for use in the procedures disclosed herein.

First And Second Embodiments

For use with heat generating means 20A or 20B, a preferred embodiment 14A of the light transmitting conduit is used. The light transmitting conduit 14A is preferably a single, flexible light transmitting fiber, such as used in fiberoptic devices, and generally has a total exterior diameter of about 600 microns or less. A single fiber generally has the rigidity needed to press the heat generating means 20A or 20B into tissue. Generally, the single light transmitting fiber or conduit 14A, which is best seen in the cross-sectional view of FIG. 7, includes a core 46 surrounded by cladding 48. The internal reflection caused by the cladding 48 is such that the optical fiber 14A has a low divergence as light exits the distal end 18A thereof. The core 46 is typically made of glass, e.g., silica quartz. The cladding 48 is typically made of silicon, plastic or silica. The core 46 and its cladding 48 have a combined diameter of less than about 0.5 millimeter to about 1.0 millimeter.

To protect the core 46 and its cladding 48, the optical fiber 14A also includes an external jacket 50 which surrounds the cladding 48 and is held in place by a resin coating 52. The external jacket 50 is usually made of a flexible plastic material such as poly(ethylene) or poly(tetrafluorethylene). It provides a flexible and smooth surface allowing easy manipulation of the medical device 10. Fiberoptic bundles are not preferred since the adhesive between individual fibers limits the amount of light which can be transmitted without melting of the bundle.

The optical fiber or light transmitting conduit 14A should be flexible, yet sufficiently resilient so that it is possible to push the same into tissue or into the tubal ostia. One such suitable optical fiber having a core diameter of 0.4 millimeters is marketed under the designation MED 400 by Quartz Products Corporation of Plainfield, N.J. Another suitable optical fiber is a 0.6 millimeter fiber commercially available under the designation HCT 600 from Ensign Bickford Co., Connecticut. The power that can be transmitted-along the fiber 14A varies with the size of the fiber. Utilizing the HCT 600 fiber, a medical device embodying this invention can transmit as much as sixty watts continuous power from an Nd:YAG laser source.

As seen in FIG. 2, the resin coating 52 and the jacket 50 have been trimmed back from the distal end 18A of the fiber 14A leaving a section of the cladding 48 surrounding fiber core 46 open to the sides. The distal end 18A of fiber 14A is shown received in place within a cavity 54 defined within the bulbous heat generating means 20A.

Figure 4:
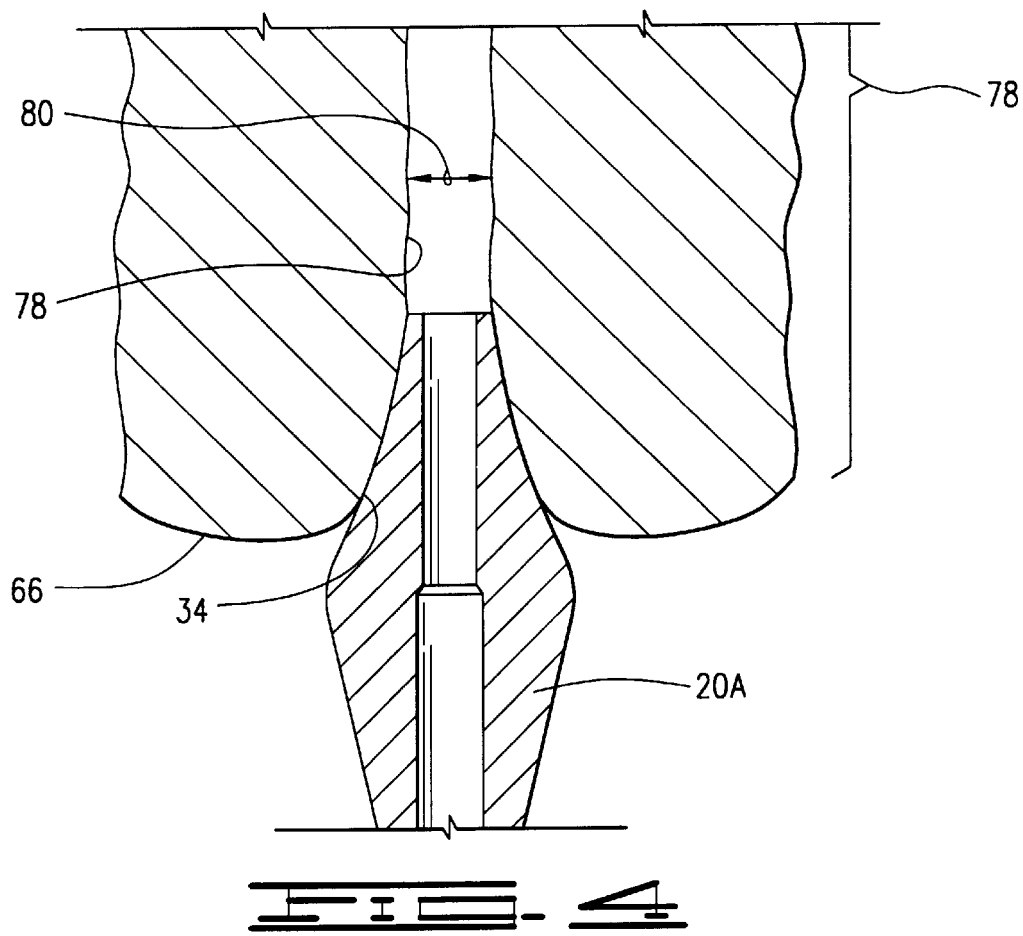
FIG. 4 is a schematic illustration of the device of FIG. 2 with its tapered forward end portion inserted into one of the patient's tubal ostia so as to center the heat applying device about the tubal ostia and against the inner wall of the patient's uterus.

The bulbous heat generating means 20A has a larger mid portion 56 with an outer diameter of at least about two millimeters. Bulbous heat generating means 20A includes a tapered forward portion 60 having an outside diameter 62 no greater than about one millimeter. As further explained below, this design permits a forward tip 64 of the tapered portion 60 to be received through one of the patient's tubal ostia with the larger portion 56 of the bulbous heat generating means 20A engaging an inner wall 66 of the uterine cavity 28 adjacent the tubal ostia 34 or 36, as best seen in FIG. 4.

As shown in FIG. 2, a longitudinal profile 66 of the first embodiment heat generating means 20A is concave. This is contrasted to the second embodiment heat generating means 20B of FIG. 3 which has its tapered forward portion 60 generally frusto-conical in shape with a straight profile 68.

The heat generating means 20A has a skirt portion 70 extending rearwardly therefrom within which is received the distal end 18A of the light transmitting conduit 14A. The skirt 70 is crimped at several locations, such as those designated as 72, to attach the heat generating means 20A to the jacket 50 of light transmitting conduit 14A. In addition, adhesive may be used between the skirt 72 and the conduit 14A.

An air space 74 is defined between the cavity 54 and the cladding 48 and resin coating 52 in the trimmed back portion of the distal end 18A of light transmitting conduit 14A. A vent 76 extends through the heat generating means 20A and communicates with the air space 74 to allow an escape aperture for gases that may develop within the cavity 54.

The heat generating means 20A includes a light transmitting aperture means 79 extending forwardly from cavity 54 through the tapered forward portion 60 to the tip 64, for enabling light energy transmitted by the conduit 14A in part to pass through the aperture means 79 into the interstitial portion of the fallopian tube associated therewith. Referring for example to FIG. 1, and to the enlarged view of FIG. 4, the junction between the fallopian tube 45 and the uterus 12 at the tubal ostia 34 includes an area extending generally through the wall of the uterus which is designated by the numeral 78 and which is generally referred to as the interstitial portion of the fallopian tube 45. The interstitial portion 78 is typically on the order of one centimeter in thickness. The tubal ostia 34 itself typically has a diameter 80 of from about 1.0 to about 2.0 millimeters.

An optically transparent means such as a lens or window 82 is positioned within the cavity 54 of bulbous heat generating means 20A so as to block the distal end of the cavity against the inflow of body fluids and tissue components. The window 82 can be made of quartz, sapphire or other optically transparent material. The aperture means 79 in the tapered portion 60 defines a communication port between the window 82 and the surrounding exterior of heat generating means 20A. The window 82 prevents bodily fluids or materials that have entered the aperture means 79 from contaminating the end of optical fiber 14A.

Light energy which is emitted from the distal end 18A of fiber 14A impinges upon a surface 84 of lens 82. Radiant energy transmitted through the conduit 14A heats the heat generating means 20A when it impinges upon the surface 84. A portion of the radiant energy, however, such as the light beam schematically illustrated as 86 passes through the window 82 and through the aperture means 79 directly into the interstitial portion 78 of tubal ostia 34.

The bulbous heat generating means 20A is preferably made of metal, such as surgical stainless steel, but could also be made of a combination of thermally conductive and thermally insulating materials, such as metals and/or ceramics. The exterior surface of the bulbous heat generating means 20A is preferably coated with a non-stick or release surface, such as poly(tetrafluorethylene), to provide easy release from the tissue. Poly(tetrafluorethylene) usually is used for operating temperatures below about 300° C.

The heat generating means 20A is preferably constructed and internally dimensioned so that the majority portion of the light energy transmitted down conduit 14A exits through aperture means 79 as the light beam 86, with a minority portion of the light energy being converted by the heat generating means 20A to heat to raise the temperature of the heat generating means 20A. This is determined by controlling the diameter of aperture means 79.

Third Embodiment

The third preferred embodiment of the heat application means 20C is shown in FIGS. 8 and 9, and as will be further described herein, forms an integral portion of the distal end 18C of the light transmitting conduit 14C.

The light transmitting conduit 14C is preferably single, flexible light transmitting fiber, such as used in fiberoptic devices, and thus is similar to light transmitting conduit 14A previously described. As with the previously described embodiments, the single light transmitting fiber or conduit 14C, best seen in FIG. 9, includes a core 100 surrounded by a cladding 102. However, conduit 14C is slightly larger and preferably has a core diameter of about 1,000 microns. The core 100 is typically made of glass, e.g., silica quartz. The cladding 102 is typically made of silicon, plastic or silica.

To protect the core 100 and its cladding 102, the optical fiber 14C normally also includes an external jacket 104 which surrounds the cladding 102 and is held in place by a resin coating. The external jacket 104 is usually made of a flexible plastic material, such as poly(ethylene) or poly(tetrafluorethylene).

As seen in FIG. 9, jacket 104 has been trimmed back from the distal end 18C of the fiber 14C, and the cladding 102 has been removed so that it extends only slightly, if at all, past jacket 104. In other words, cladding 102 and jacket 104 may be removed to the same point, or the cladding may extend slightly outwardly from the jacket.

Distal end 18C is uniquely formed to include an integral orb or bulb portion 106. A cylindrical portion 108 may extend outwardly therefrom. Cylindrical portion 108 is preferably the samediameter as, and is coaxial with, the main portion of core 100. Orb portion 106 is integrally formed, so it is made of the same material as the rest of core 100.

A portion of the outer surface. of distal end 18C is frosted, and this area includes the outside diameter of cylindrical portion 108 and an outwardly facing half of orb 106. Thus, the frosted area extends from the outermost end 110 of cylindrical portion 108 to about a generally equatorial area 112 on orb portion 106. This frosted area may be referred to as a nose portion. Outermost end 110 of cylindrical portion 108 is polished clear and smooth.

The frosted area prevents or reduces reflection of light energy back up fiber 14C, as will be further discussed herein. The frosted area also serves as an indicia means for indicating the position of heat application means 20C, and this will also be discussed further herein.

Outside diameter 114 of orb portion 106 is preferably approximately twice the size of outside diameter 116 of cylindrical portion 108. That is, in the preferred embodiment, outside diameter 114 of orb portion 106 is approximately 2,000 microns, and the outside diameter 116 of cylindrical portion 108 is approximately 1,000 microns. While orb portion 106 is shown as generally spherical, this is not absolutely necessary, and orb portion 106 may have an ellipsoid shape. The important aspect is that orb portion 106 is an enlarged part of distal end 18C of conduit 14C.

In an alternate embodiment, only orb portion 106 is present, and there is no cylindrical portion extending therefrom. In this embodiment, a flat surface is formed on the outwardly facing side of orb portion 106. This flat surface is polished clear and smooth in a manner similar to end 110 of cylindrical portion 108. The flat surface may have an outside diameter approximately equal to the diameter of the main portion of light transmitting conduit 14C.

In forming distal end 18C, the following procedure is generally followed. The light transmitting fiber is supplied and cut to an approximate length. Jacket 104 is stripped a desired length from an end of the fiber. Cladding 102 is removed preferably by application of heat, such as a flame. The cladding is removed so that the material thereof will not mix with the material of core 100 when orb portion 106 is molded.

Figure 11:
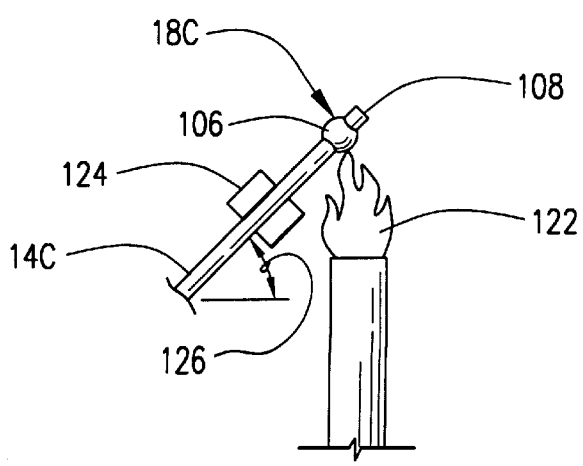
FIG. 11 schematically illustrates a method of making the third embodiment heat applying device shown in FIGS. 8 and 9.

After cladding 102 has been removed, leaving the desired length of bare core 100, heat is applied, such as by a flame 122, to distal end 18C. See FIG. 11. The material of core 100 is thus melted to form orb portion 106. In the preferred embodiment, but not by way of limitation, the fiber is held in a jig 124 at an angle 126 to the flame 122 and rotated so that the melting of the material of core 100 and the formation of orb portion 106 is substantially uniform. The angle 126 of the fiber to the flame is preferably in the range from about 45° to about 60°.

After cooling, distal end 18C, a step of preliminary polishing is carried out. This polishing not only smooths the outer surface of the exposed portion of core 100, including orb portion 106 and cylindrical portion 108, but also insures accurate sizing of the outside diameter of orb portion 106. Checking of the sizing may be made in a manner known in the art.

After the preliminary polishing step, the cylindrical portion 108 (if any) and the outermost half of the orb portion 106 are etched with a glass etching material to frost the surface as previously described.

The final step in preparation of distal end 18C is to polish outermost end 110 of cylindrical portion 108 (or to polish the flat surface on orb portion 106 if there is no cylindrical portion 108) to form a light transparent aperture means 118. A laser connector is attached to the other end of the length of fiber 14C, either before or after the molding of the tip.

The light transparent aperture means 118 faces outwardly on distal end 18C and is adapted for enabling light energy transmitted by the conduit 14C in part to pass through the aperture means 118 into the interstitial portion of the fallopian tube associated therewith.

Because heat application means 20C is a single integral portion of distal end 18C, there is no potential problem of bodily fluids or materials entering this third embodiment of the apparatus and contaminating it.

Radiant energy transmitted through the conduit 14C enters heat application means 20C. Because the material of core 100 is a multi-mode material, some of the radiant energy will reflect therein. The previously described frosted area on heat application means 20C eliminates or greatly reduces the reflection of light energy back up conduit 14C where it would otherwise be lost. The result is that the orb portion 106 absorbs some light energy, and there is a slight thermal buildup. However, this thermal buildup is only less than about 10° F. and thus not medically significant. That is, the thermal buildup in the orb portion 106 is not enough to cause a tissue reaction by conduction when heat application means 20C is placed in contact therewith. In other words, if light energy were transmitted through heat application means 20C when the device was not in the body of a patient, any heating by the light energy of heat application means 20C would be negligible. This is distinguished from the first and second embodiments of the present invention in which heat generating means 20A and 20B are significantly heated by the light energy transmitted through conduit 14A.

The unfrosted, polished half of orb portion 106 allows some of the light energy to escape the orb portion. This insures that the orb portion 106 does not have too much thermal buildup.

However, when heat application means 20C is placed in contact with a portion of the patient's body, as shown in FIG. 1 and FIG. 4, some light energy is transmitted through the frosted surface to the contacted portions of the body and this transmission of light energy, rather than heat conduction, heats those body portions. This is a result of the differential in the light index between the material of conduit 14C and the human tissue adjacent thereto. So, while heat application means 20C itself is not heated, it applies heat to the adjacent tissue by transmitting light energy to the tissue portions it contacts.

The construction of heat application means 20C is thus such that the majority portion of the light energy transmitted down 14C exits through aperture means 118 as a light beam 120 (see FIG. 9). A minority portion of the light energy is transmitted through the outside diameter of cylindrical portion 108 and through at least a portion of orb portion 106.

Laser Light Source

Referring again to FIG. 1, a laser light source 88 is connected to the proximal end 16 of light transmitting conduit 14. This connection is identical in all of the previously described embodiments. There are several laser sources which could be used. First, the preferred laser source is a Neodymium-Yttrium Aluminum Garnet (Nd:YAG) laser having a characteristic wavelength of 1064 nanometers. The laser light source 88 preferably is an Nd:YAG laser light source such as for example a Trimedyne 1,000 OptiLase™ as marketed by. Trimedyne, Inc., of Santa Ana, Calif. Also, a KTP 532 laser which is an Nd:YAG laser modified to double the frequency and thus provide a characteristic wavelength of 532 nanometers may be used. A third choice is an argon gas laser having a characteristic wavelength of either 488 or 512 nanometers.

The laser 88 produces the light which is transmitted through the heat application means 20 to provide heat as previously described. The word "light" is used in its broad sense, meaning electromagnetic radiation which propagates through space and includes not only visible light, but also infrared, ultraviolet and microwave radiation.

A beam splitter 90 may be placed in laser transmitting conduit 14 with a further light transmitting conduit 92 connecting the same to a pyrometer 94 in order to monitor the temperature of heat generating means 20A and 20B of the first and second embodiments.

Sterilizinq Procedures

Figure 10:
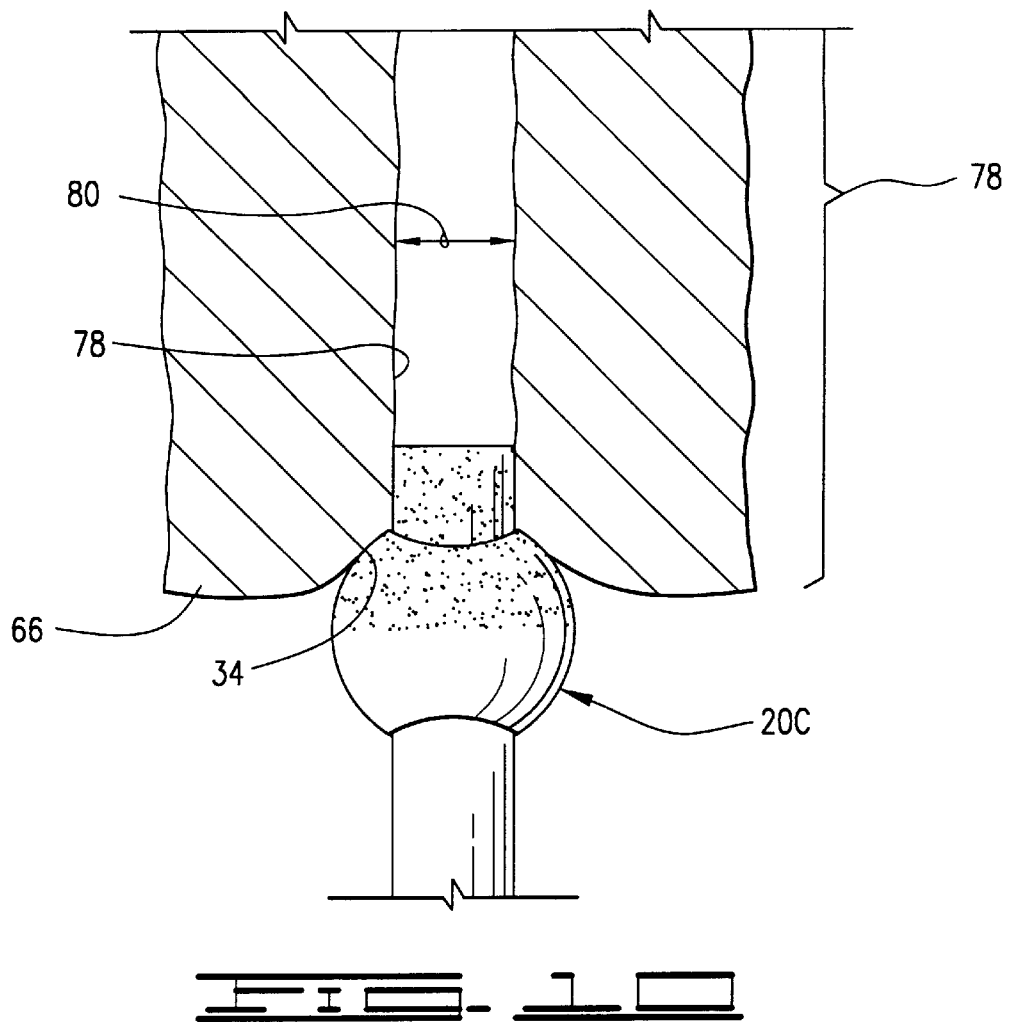
FIG. 10 is a schematic illustration of the device of FIGS. 8 and 9 with a cylindrical forward end portion inserted into one of the patient's tubal ostia and with the orb portion against the inner wall of the patient's uterus so as to center the heat applying device about the tubal ostia and against the inner wall of the patient's uterus.

The preferred procedures for sterilizing a human female patient will now be described primarily with reference to FIGS. 1, 4 and 10. FIG. 4 is an enlarged view of the area surrounding the left tubal ostia 34 of FIG. 1 showing the first embodiment heat generating means 20A in place adjacent thereto. Second embodiment heat generating means 20B is positioned similarly. FIG. 10 is an enlarged view of the area surrounding the left tubal ostia 34 of FIG. 1 showing the third embodiment heat application means 20C in place adjacent thereto.

The methods of sterilizing a female patient generally include a first step of inserting into the patient's uterus 12 an elongated energy transmitting conduit 14 having the heat application means 20 on the distal end 18 thereof.

The heat application means 20 is maintained in fixed contact with an inner wall 66 of the patient's uterus 12 adjacent the tubal ostia 34 for a sufficient time and while transmitting sufficient energy to the heat application means to coagulate a substantial part of the interstitial portions 78 of the patient's fallopian tube 45 so that the fallopian tube 45 is closed. Subsequently, the procedure is repeated for the patient's second fallopian tube 47.

The procedures of the present invention differ in several significant aspects from the use of somewhat similar apparatus in connection with endometrial ablation procedures.

First, in the present procedure, the heat application means is maintained in fixed contact with the tissue adjacent the tubal ostia for a substantial time, whereas in endometrial ablation procedures there is no significant fixed contact with any portion of the tissue, but rather there is a continuous movement of the laser fiber and/or heated tip across the tissue or a short distance away from the tissue so as to cover very large areas of tissue. The present procedure relies on a fixed contact of the heat application means 20 with the tissue adjacent the tubal ostia for a substantial time, preferably at least ten seconds, while transmitting energy through the conduit 14.

In the first and second embodiments, the bulbous heat generating means 20A or 20B is heated to a relatively high temperature whereby heat is transmitted to the tissue through direct contact, and additionally that portion of the light energy transmitted out the aperture means 79 passes into the interstitial portion of the fallopian tube to aid in coagulating the same. Thus, in the first and second embodiments, there is a combination of heat conduction from the bulbous heat generating means 20A or 20B into the tissue, and radiant light energy passing through the aperture means 79 and falling directly upon the tissue defining the inner surface of the interstitial portion 78 of the fallopian tube 45. As previously mentioned, it is preferred that a majority of the light energy is passed through the aperture means 79 as radiant energy.

Endometrial ablation also uses much higher power settings than used in the present sterilization procedure. Typical endometrial ablations procedures use a sixty watt power setting wherein the present procedure preferably only uses about fifteen watts. Fifteen watts would not be enough to accomplish the endometrial ablation because it would not affect the tissue deep enough with the relatively short duration of exposure of the laser to any one area of the tissue in an endometrial ablation procedure.

The geometry of first and second embodiment heat generating means 20A and 20B, shown in FIGS. 2 and 3, is very important in the proper placement of the heat generating means adjacent the tubal ostia 34. The tapered forward portion 60 of first and second embodiments 20A and 20B is inserted through the tubal ostia 34, thereby centering the heat generating means 20A or 20B about the tubal ostia against the inner wall 66 of the uterine cavity. Thus, the aperture means 79 is also centered within the interstitial portion 78 of the fallopian tube so as to direct the radiant laser light energy directly into the fallopian tube.

The geometry of the third embodiment heat application means 20C shown in FIGS. 8 and 9, is also important in the proper placement of the heat generating means adjacent the tubal ostia. The cylindrical portion 108 and orb portion 106 are inserted through the tubal ostia, as seen in FIG. 10, thereby centering the heat application means 20C about the tubal ostia 30 against the inner wall 66 of the uterine cavity 28. The demarcation between the frosted and polished areas of orb portion 106 provides an indicia means for helping the surgeon to properly position the device. If there is no cylindrical portion 108, orb portion 106 is still inserted through the tubal ostia in the same general manner as shown in FIG. 10, and this generally centers the orb portion 106 about the tubal ostia 30 against the inner wall 66 of the uterine cavity. Thus, with or without cylindrical portion 106, the aperture means 118 is also centered within the interstitial portion 78 of the fallopian tube so as to direct the radiant laser light energy directly into the fallopian tube.

Utilizing the preferred Nd:YAG laser light source 88, it has been determined that the heat application means 20 is preferably maintained in fixed contact with a patient's uterus adjacent the tubal ostia, as shown in FIGS. 4 and 10, for a time in the range of from about ten to about forty-five seconds while simultaneously transmitting laser energy from the source 88 through the conduit 14 at a rate in the range of about ten to about twenty-five watts. More preferably, the heat application means 20 is maintained in fixed contact with the uterus for a time in the range of about fifteen to about thirty seconds while simultaneously transmitting laser energy at a rate in the range of from about fifteen to about eighteen watts. It appears that an optimum setting is about fifteen watts for about thirty seconds.

The amount of energy transmitted to the heat application means 20 is chosen so as to result in the heating of the tissue making up the interstitial portion 78 of the fallopian tube 45 to a temperature above about 70° C. so that protein in the tissue is coagulated and less than about 100° C. so as prevent vaporizing of the tissue. It will be appreciated that too high a temperature, which vaporizes the tissue, would destroy the tissue, creating a hole, which is of course undesirable. The desired result is to coagulate the tissue so that the interstitial portion 78 of the fallopian tube 45 or 47 will be closed by altered scar type tissue.

EXAMPLE 1

Figure 5:
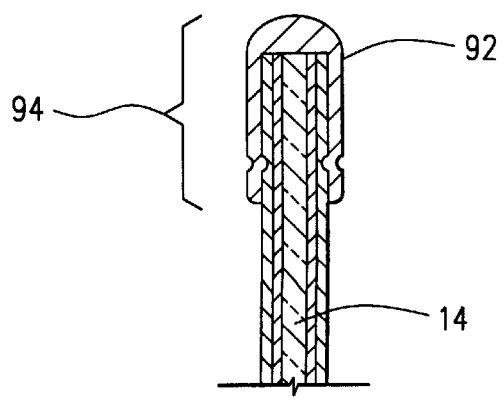
FIG. 5 is a cross-sectional view of a generally cylindrical heat generating means, which itself is part of the prior art.

The first clinical trial of sterilization procedures utilizing laser energy was conducted utilizing the prior art device illustrated in FIG. 5 which differs somewhat from the preferred embodiments of the present invention shown in FIGS. 2, 3, 8 and 10 which have been subsequently developed. The device of FIG. 5 includes the light transmitting conduit 14 having a heat generating device 92 attached to the distal end thereof. The device 92 is generally cylindrical in shape and an entire length 94 thereof has a diameter of no greater than about one millimeter. The device 92 may be constructed for example as shown in FIG. 2 of U.S. Pat. No. 4,773,413, or may be any other commercially available heat generating tip having the generally cylindrical geometry just described. Four patients were treated. All patients underwent laparoscopic tubal sterilization in the 'standard fashion with bipolar electrocautery at the distal portion of the fallopian tube. With simultaneous observation through the laparoscope, a hysteroscope was introduced into the uterine cavity and a one millimeter temperature control probe, such as probe 92, was placed through the hysteroscope and guided into the ostia of the fallopian tube as schematically illustrated in FIG. 6. An HGM Argon Model 20S laser source was used. Temperature settings were varied from 150° C. to 400° C. with five second pulses varying in number from two to fifty. Heat was applied to the tissue at a plurality of locations, as indicated in phantom lines in FIG. 6 as 92A, 92B and subsequently 92C, along the fallopian tubes, a first one of the locations 92A being located the greatest distance into the tube, and subsequent locations 92B and 92C being successively closer to the patients' uterine cavity. Three months following treatment, a hysterosalpingogram demonstrated three oviducts were blocked at the cornual portion of the uterus as was anticipated, and five others were opened to the distal segment of the bipolar electrocautery area. After reviewing the data, it would appear that those successful procedures in which the cornua was blocked were associated with the multiple pulses and higher temperature settings on the laser. It appears from these results that with proper timing and temperature settings, the procedure just described could reliably sterilize the patient. It was determined, however, that the procedure illustrated in FIG. 6 was not the preferred procedure, because of difficulties for the physician in manipulating the instrumentation involved. A further significant observation from this data is that it appears unlikely that prior art endometrial ablation procedures such as those reported by Goldrath and Daniell et al., as discussed above, actually resulted in closing of the fallopian tubes; instead, it appears most likely that the sterilization procedure observed in patients subjected to an endometrial ablation procedure is a result of the destruction of the endometrium rather than the closing of the fallopian tubes. Once the endometrium is destroyed, the patient will be rendered sterile even though the fallopian tubes are still open, because there is no place for a fertilized egg to attach itself to the uterine lining. Since even the least sensitive of the trials that were conducted would result in more intense localized heating than would the endometrial ablation procedures, it appears unlikely that endometrial ablation procedures consistently result in closing of the fallopian tubes.

EXAMPLE 2

Subsequent to the work described in Example 1, it was determined that a much easier procedure for the physician would be one in which it was not necessary to actually insert the heated device into the fallopian tube, but rather to merely place it adjacent the fallopian tube. A subsequent set of clinical tests was performed on three patients utilizing a heated device like that illustrated in FIG. 10 of U.S. Pat. No. 4,773,413 to Hussein et al., marketed by LaserControl Medical Systems Division of Trimedyne, Inc., under the designation SpectraProbe™-80. The SpectraProbe™-80 device is designed so that eighty percent of the laser energy transmitted thereto exits through the forward aperture thereof with the remainder being converted to heat, raising the temperature of the device.

The SpectraProbe™-80 device, as illustrated in FIG. 10 of U.S. Pat. No. 4,773,413 does not have a forward tip, either elongated or cylindrical, but instead has a rounded forward bulbous surface. The SpectraProbe™-80 was utilized on three patients utilizing a Cooper Model 8,000 Nd:YAG laser. The tests were run at a variety of time and power settings to observe the effect of utilizing various amounts of energy, as set forth in the following descriptions.

Patient A

This patient was placed in a semi-lithotomy position, prepped with Betadine Scrub and draped in sterile linens in the usual manner for a laparoscopic procedure. A one-centimeter incision was made below the umbilicus. Verres needle was instilled approximately three liters. Pelvic cavity was visualized. The fallopian tube on the left was identified and fulgurated near the fimbriated end of the fallopian tube. The right tube was adherent up under some omentum and other adhesions. Therefore, it was fulgurated approximately two centimeters from the cornua. Following this, the laparoscope was left in place, and the hysteroscope was placed after dilating the cervix to a size twenty Heany dilator. An eight-millimeter hysteroscope was placed. A SpectraProbe™-80 tip was placed through the hysteroscope and placed adjacent the left cornual ostia and was fired at fifteen watts for thirty seconds. Blanching was noted on the fundal side of the surface, and the SpectraProbe™-80 tip was noted to be near the surface of the fundus. Some fluid exuded through the thin portion of the fundus at that point. No further bleeding was encountered. The laser probe was removed, and a one-millimeter heat probe was inserted and attached to a Model 20S Argon Laser and was placed in the os on the right side and fired at 400° C. for five seconds on three occasions. The procedure was terminated. The laparoscopic incision was reexamined. No abnormal bleeding appeared to be present. The one area on the sigmoid colon had a bloody patch to it. It did not appear to have any blanching consistent with any type of laser energy impact. The surface was washed copiously with saline and appeared to have a superficial wound. No active bleeding was encountered. Also, adhesions were noted on initial entry of the laparoscope and these adhesions were fulgurated with bipolar cautery and cut with sharp scissors. This was to visualize the pelvis on initial entry of the laparoscope. $CO_2$ was allowed to escape. Incisions were closed with subcuticular suture of 4-0 Vicryl, and the patient was taken to the recovery room in good condition. Estimated blood loss was less than 5 cc. Note that this first patient had the procedure like that of FIG. 6 on the right side as a comparison to the newer procedure which was used on the left side. Three months later a hysterosalpingogram showed both ostia to be closed.

Patient B

The patient was placed in a semi-lithotomy position and prepped with Betadine Scrub and draped with sterile linens in the usual manner for laparoscopic procedure. A one-centimeter incision was made below the umbilicus, and a Verres needle was instilled approximately three liters. The ten-millimeter trocar was introduced through the same incision. The pelvic cavity was visualized, and the six-millimeter trocar was introduced through the lower mid-line incision. The bowel was pushed up out of the pelvis with a blunt probe. The uterus was noted to be retroflexed and slightly enlarged. The fallopian tubes were identified, fulgurated at their distal end on either side with bipolar electrocautery without difficulty. Following this the uterus was sounded to eight centimeters and noted to be retroflexed and somewhat irregular, dilated to size #18 Heany dilator. The intrauterine cavity was visualized. The right ostia was identified, and the SpectraProbe™-80 tip was placed in the osteal opening. The laser was turned on at fifteen watts for thirty seconds. The opposite ostia was then identified on the left side, and the SpectraProbe™-80 tip was placed in the os and fired to fifteen watts for fifteen seconds. The patient tolerated the procedure well, and no unusual bleeding was encountered. Instruments were removed. The $CO_2$ was allowed to escape. The incisions were closed with subcuticular sutures of 40-Vicryl. Three months later, a hysterosalpingogram showed both ostia to be closed.

Patient C

The patient was placed in the lithotomy position, prepped with Betadine Scrub and draped with sterile linens for laparoscopy procedure. A one-centimeter incision was made below the umbilicus. A Verres needle was instilled approximately three liters. A ten-millimeter trocar was introduced through the same incision. The pelvic area was visualized, and the six-millimeter trocar was introduced through a lower mid-line incision. The fallopian tubes were identified and fulgurated at the distal portion with bipolar electrocautery on either side without difficulty. Following this, the laparoscope was left intact, and the hysteroscope was placed through the cervix after dilating it to a size #18 Heany dilator. It was somewhat difficult to visualize the ostia in this patient, on the left side particularly. The right side was more easily seen. A SpectraProbe™-80 tip was placed at the ostial opening and fired for thirty seconds at eighteen watts. This was carried out in the same exact fashion on the opposite side while under direct vision through the laparoscope. By second person, blanching was noted to appear at the cornual portions on both sides without difficulty. There were no further abnormalities noted. The instruments were removed, and the incisions abdominally were closed with a subcuticular stitch of 4-0 Vicryl. Three months later a hysterosalpingogram showed the left ostia (which had been difficult to locate) to be open, and showed the right ostia to be closed.

On Patients A and B, Lupron Depo 3.75 milligrams was given preoperatively on the third day of the menstrual cycle. Lupron is a gonadotropin releasing hormone agonist which stops all hormone production of the ovaries and therefore Estrogen production. This stops simulation of the endometrium which makes the tissue thinner and allows better visualization of the ostia.

In summary re Example 2, of the five tubal ostia treated with the SpectraProbe™-80 tip, four were closed by the procedure. The one which was not (left side of Patient C) had been difficult to locate. Also, Patient C had not received the Lupron preoperatively. Several conclusions can be made from these results. First, the procedure utilizing a heated tip placed against the tubal ostia with a portion of the laser energy directed through an aperture into the fallopian tube appears to be successful; four out of five tests were successful, with the failure of the fifth being explained by difficulty in locating the tubal ostia. Second, the difficulty encountered in locating the left tubal ostia of Patient C and placing the heated device adjacent thereto illustrates the desirability of a tip having an elongated forward portion, such as illustrated in FIGS. 2, 3, 8 and 9, to aid in accurately placing the device centered against the tubal ostia. Third, the desirability of the preoperative Lupron medication is illustrated to aid in the subsequent visualization of the tubal ostia.

It is believed that the procedures set forth herein provide many advantages as compared to present day sterilization procedures. Most significantly, these procedures are capable of being administered on an out-patient basis with no need for general anesthetic.

Thus, it is seen that the apparatus and methods of the present invention readily achieve the ends and advantages mentioned as well as those inherent therein. While certain preferred embodiments of the invention have been disclosed and described for purposes of the present disclosure, numerous changes may be made by those skilled in the art which changes are encompassed within the scope and spirit of the present invention as defined by the appended claims.

What is claimed is:

1. A method of sterilizing a female patient, said method comprising the steps of:
    (a) inserting into the patient's uterus an elongated light transmitting conduit having a distal end with an integrally formed enlarged portion thereon;
    (b) contacting said distal end of said conduit with tissue adjacent to a fallopian tube of the patient such that at least a forward portion of said enlarged portion is received within a corresponding tubal ostia and centered about said tubal ostia; and
    (c) transmitting light energy through said conduit such that a substantial part of an interstitial portion of the fallopian tube is coagulated so that the fallopian tube is closed.

2. The method of claim 1 further comprising the step of:
    (d) repeating steps (b) and (c) for the other of the patient's fallopian tubes, so that both fallopian tubes are closed.

3. The method of claim 1 wherein:
    step (a) is further characterized by said distal end having a light transmitting aperture thereon; and
    at least a portion of said light energy is transmitted through said light transmitting aperture.

4. The method of claim 3 wherein said portion of said light energy is a majority portion of the light energy transmitted through said conduit.

5. The method of claim 3 wherein another portion of said light energy is transmitted through said enlarged portion.

6. The method of claim 1 wherein:
    step (a) is further characterized in that said distal end has an elongated portion extending outwardly from said enlarged portion; and
    step (b) includes a step of inserting at least said elongated portion into the patient's fallopian tube.

7. A method of sterilizing a female patient, said method comprising the steps of:
    (a) inserting into the patient's uterus an elongated light energy transmitting conduit having an enlarged portion on a distal end thereof, said distal end having a light transmitting aperture extending through a forward portion thereof;
    (b) positioning said forward portion of said device adjacent one of the patient's tubal ostia so that the device is centered about said one tubal ostia and held in fixed contact with the patient's uterus;
    (c) transmitting light energy through said conduit to said device, passing a first portion of said energy through said aperture into the patient's fallopian tube associated with said one tubal ostia, and passing a second portion of said energy through said enlarged portion, said first and second portions of said light energy being sufficient in combination to cause said fallopian tube to be closed due to alteration of the tissue thereto.

8. The method of claim 7 further comprising:
    (d) repeating steps (b) and (c) for the patient's other tubal ostia and associated other fallopian tube.

9. The method of claim 7 wherein:
    step (a) is further characterized by said distal end having an elongated portion extending from said enlarged portion and said light transmitting aperture being on an outwardly facing end of said elongated portion; and
    step (b) further comprises the step of inserting at least said elongated portion into the patients' fallopian tube.

10. The method of claim 7 wherein steps (b) and (c) result in the heating of tissue making up the interstitial portion of the fallopian tube to a temperature above about 70° C. so the protein in the tissue is coagulated and less than about 100° C. so that vaporization of the tissue is prevented.

11. A method of sterilizing a female patient, said method comprising the steps of:
    (a) providing an elongated light transmitting conduit comprising an optical fiber, said optical fiber comprising:
        a proximal end adapted for connection to a light energy source;
        a distal end;
        an enlarged portion integrally formed on said distal end; and
        an elongated portion integrally formed on said distal end and extending distally from said enlarged portion, said elongated portion having an aperture thereon;
    (b) inserting said light transmitting conduit into the patient's uterus;
    (c) contacting said distal end of said conduit with tissue adjacent to a fallopian tube of the patient such that said elongated portion extends at least partially into the fallopian tube and at least a forward portion of said enlarged portion is received within a corresponding tubal ostia and centered about said tubal ostia; and
    (d) transmitting light energy through said conduit with at least a portion of said light passing through said aperture, such that a substantial part of an interstitial portion of the fallopian tube is coagulated whereby the fallopian tube is closed.

12. The method of claim 11 further comprising the step of:
    (e) repeating steps (c) and (d) for the other of the patient's fallopian tubes, so that both fallopian tubes are closed.

13. The method of claim 11 wherein said portion of said light energy passing through said aperture is a majority portion of the light energy transmitted through said conduit.

14. The method of claim 11 wherein another portion of said light energy is transmitted through said enlarged portion.

15. The method of claim 11 wherein said elongated portion is substantially cylindrical.

16. The method of claim 11 wherein said aperture is a polished, outwardly facing end of said elongated portion.

17. The method of claim 11 wherein steps (c) and (d) result in the heating of tissue making up the interstitial portion of the fallopian tube to a temperature above about 70° C. so that the protein in the tissue is coagulated and less than about 100° C. so the vaporization of the tissue is prevented.

* * * * *